United States Patent [19]
Sivaraja et al.

[11] Patent Number: 6,043,038
[45] Date of Patent: Mar. 28, 2000

[54] HIGH-THROUGHPUT SCREENING ASSAYS FOR MODULATORS OF PRIMASE ACTIVITY

[75] Inventors: Mohanram Sivaraja, Palo Alto; Ashok Sanadi, Sunnyvale; M. Gregory Peterson, Millbrae, all of Calif.

[73] Assignee: Tularik, Inc., South San Francisco, Calif.

[21] Appl. No.: 09/052,924

[22] Filed: Mar. 31, 1998

[51] Int. Cl.[7] .............................. C12Q 1/68; C12P 19/34; C07H 21/02; C07H 21/04

[52] U.S. Cl. .................... 435/6; 435/5; 435/91.2; 435/91.21; 435/91.5; 536/23.1; 536/24.3; 536/24.31; 536/24.32; 536/24.33; 530/350

[58] Field of Search .................... 435/6, 5, 91.2, 435/91.21, 91.5; 536/23.1, 24.3, 24.31, 24.32, 24.33; 530/350

[56] References Cited

U.S. PATENT DOCUMENTS 5,360,714  11/1994  Seeger .......................................... 435/5
5,413,906  5/1995  Eberle et al. ................................ 435/5

OTHER PUBLICATIONS

Sano et al, "Comparable sensitivities for detection of HIV–1 reverse transcriptase and other polymerases by RT assays requiring no radioisotopic materials", J. Virol. Methods 53:235–244, 1995.
Ballard (1982) *Mol. Immunol.* 19:793–799.
Blais (1994) *Appl. Env. Microbiol.* 60:348–352.
Bogulavski et al. (1986) *J. Immunol. Methods* 89:123–130.
Casebolt, et al. (1992) *J. Clin. Microbiol.* 30(3):608–612.
Catapano et al. (1991) *Cancer Res.* 54:1829–1835.
Coutlee et al. (1989) *Analytical Biochemistry* 181:153–162.
Fliss et al. (1993) *Appl. Env. Microbiol.* 59(8):2698–2705.
Fliss, et al. (1955) *Appl. Microbiol. Biotechnol.* 43:717–724.
Griep (1995) *Indian J. Biochem Biophys* 32(4):171–8.
Hirose et al. (1985) *Biochem. and Biophys. Res. Comm.* 132:210–216.
Kiney et al. (1989) *J. Clin. Microbiol.* 27:6–12.
Kuchta (1996) *Methods in Enzymology* 275:241–257.
Miller, et al. (1988) *J. Clin. Microbiol.* 26(7):1271–1276.
Newman, et al. (1989) *Mol. and Cellular Probes* 3:375–382.
Palf et al. (1990) *Biochemistry* 29:3442–3450.
Pisetsky and Caster (1982) *Mol. Immunol.* 19:645–650.
Prooijen–Knegt (1982) *Exp. Cell Res.* 141:397–407.
Rudkin (1976) *Nature* 265:472–473.
Sheaff (1993) *Biochemistry* 32(12):3027–37.
Sheaff et al. (1994) *Biochemistry* 33:2247–2254.
Stollar (1970) *PNAS* 65:993–1000.
Swart et al. (1995) *Biochemistry* 34:16097–16106.
Tseng et al. (1977) *Cell* 12:483–489.
Viscidi et al. (1989) *J. Clin. Microbiol.* 27(1):120–125.
Yagura et al. (1987) *Biochemistry* 26:7749–7754.
Yoshida et al. (1985) *J. BioChem.* 98:427–433.

*Primary Examiner*—Jeffrey Fredman

[57] ABSTRACT

This invention provides novel assays for primase activity and for identifying modulators of primase activity. The assays include both solid-phase and liquid-phase methods that are amenable to high throughput screening methods. The assays of the invention are readily adaptable to numerous types of primase, and are capable of identifying novel classes of primase activity modulators.

28 Claims, 2 Drawing Sheets

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 68 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: modified_base
      (B) LOCATION: 1
      (D) OTHER INFORMATION: /mod_base= OTHER
          /note= "N = 5' NH-2-adenosine"

(xi) SEQUENCE DESCRIPTION: SEQ ID NO:1:

NAAAAAAAAA AAAAAAAACT TCTTCCCTTC CTACTACCCT CCCGCTCTTC CTCTCTTCTT    60

TCTCCTTT    68

(2) INFORMATION FOR SEQ ID NO:2:

(i) SEQUENCE CHARACTERISTICS:
      (A) LENGTH: 42 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: modified_base
      (B) LOCATION: 1
      (D) OTHER INFORMATION: /mod_base= OTHER -continued /note= "N = 5' NH-2-guanosine"

(xi) SEQUENCE DESCRIPTION: SEQ ID NO:2:

NGACGGCGAA AGCCGCCGTC CCTACTGCAA AGCCAAAAGG AC                42

HIGH-THROUGHPUT SCREENING ASSAYS FOR MODULATORS OF PRIMASE ACTIVITY

CROSS-REFERENCE TO RELATED APPLICATION

This application is related to commonly assigned U.S. patent application Ser. No. 08/882,606, filed Jun. 25, 1997, now abandoned which application is incorporated herein by reference in its entirety.

FIELD OF THE INVENTION

This invention pertains to the field of assays for determining nucleic acid primase activity. Both solid phase and solution phase assays are provided. The assays are useful for high throughput screening of compounds for ability to modulate primase activity.

BACKGROUND OF THE INVENTION

Many clinically important agents that are used to combat a wide variety of conditions are directed at inhibiting DNA replication. Inhibition of DNA replication can not only prevent proliferation of an infecting pathogen, but can also prevent proliferation of cancer cells. Typically, presently available agents inhibit DNA replication by interfering with DNA polymerases. A significant disadvantage of many of these agents is that DNA polymerases are often involved in cellular processes other than DNA replication, such as DNA repair. Another disadvantage that is sometimes observed is a lack of specificity for a particular target organism; such agents can inhibit desirable DNA replication of host cells, as well as replication in the target organism.

The shortcomings of many presently available agents for inhibiting DNA replication demonstrates the need for agents that inhibit DNA replication by a mechanism other than interference with DNA polymerase. One target of interest is primases, which are enzymes that catalyze the polymerization of an RNA oligonucleotide on a DNA template. These short oligonucleotides act as primers for DNA polymerases, which are not capable of initiating synthesis of a DNA strand de novo. Because of the critical functions played by primases, they provide promising targets for therapeutic intervention in, for example, pathogenic infection and cancer. For example, many large DNA viruses such as the herpes viruses have specific, targetable primases for which it would be desirable to develop specific inhibitors that do not interfere with primases of the infected organism.

The search for modulators of primases has been severely hampered by shortcomings with previously available assay methods. The standard assay for measuring primase activity uses solution-phase radiolabel incorporation and gel electrophoresis to monitor, directly or indirectly, the polymerization of nascent RNA oligonucleotides (see, Yoshida et al. (1985) *J. BioChem.* (Tokyo) 98: 427–433). Unfortunately, this assay is time-consuming, cumbersome and poorly suited to high-throughput drug screening. Detection of primase-synthesized primers in whole cell assays is difficult because the primers typically make up less than about one percent of the total cellular RNA (Tseng et al. (1977) *Cell* 12: 483–489; Palf et al. (1990) *Biochemistry* 29: 3442–3450). A more recently developed assay method uses whole cell lysates and involves isolating nuclear matrices (Catapano et al. (1991) *Cancer Res.* 54: 1829–1835). This method, however, is also not suitable for high-throughput drug screening because a density gradient centrifugation step is required in order to purify the primase-synthesized primers. Thus, a need exists for new primase assays that are suitable for use in high-throughput screening methods. The present invention satisfies this and other needs.

SUMMARY OF THE INVENTION

The invention provides high throughput methods and related compositions for measuring nucleic acid primase activity. Both solution phase and solid phase assays are provided. The solution phase assay methods involve incubating a reaction mixture comprising a DNA template, a primase, and ribonucleotide triphosphates under conditions whereby the primase, if present, polymerizes the triphosphates on the template to form a nucleic acid comprising one or more DNA-RNA heterohybrid regions. The nucleic acid is contacted with a recognition reagent that comprises a tag and a moiety which specifically binds to a DNA-RNA heterohybrid region. The tag is bound to a solid support, thus immobilizing the nucleic acid on the solid support. The presence or absence of DNA-RNA heterohybrid regions on the solid support is then detected.

The solid phase primase assays of the invention involve providing a DNA primase template that is pre-immobilized on a solid support. The DNA template is contacted with a reaction mixture that includes a primase and ribonucleotide triphosphates under conditions whereby the primase, if present, polymerizes the triphosphates on the template to form a nucleic acid comprising one or more DNA-RNA heterohybrid regions. The presence or absence of DNA-RNA heterohybrid regions bound to the solid support is then detected.

In some embodiments of both the solution phase and solid phase assays, the presence of DNA-RNA heterohybrid regions is detected by contacting the nucleic acid with a detection reagent which binds to the DNA-RNA heterohybrid regions. The amount of detection reagent bound to the DNA-RNA heterohybrid regions is then determined. In other embodiments, the heterohybrid regions are detected by including in the reaction mixture at least one of the ribose nucleotide triphosphates that comprises a label, such as biotin or digoxigenin. A detection reagent that specifically binds the label is used to detect the presence or absence of DNA-RNA heterohybrid regions.

The invention also provides methods for identifying modulators of primase activity. These methods involve performing the assay methods in the presence and absence of a potential primase activity modulator. A difference in the amounts of measured heterohybrid regions indicates that the agent modulates the activity of the primase.

DETAILED DESCRIPTION

Definitions

Figure 1:
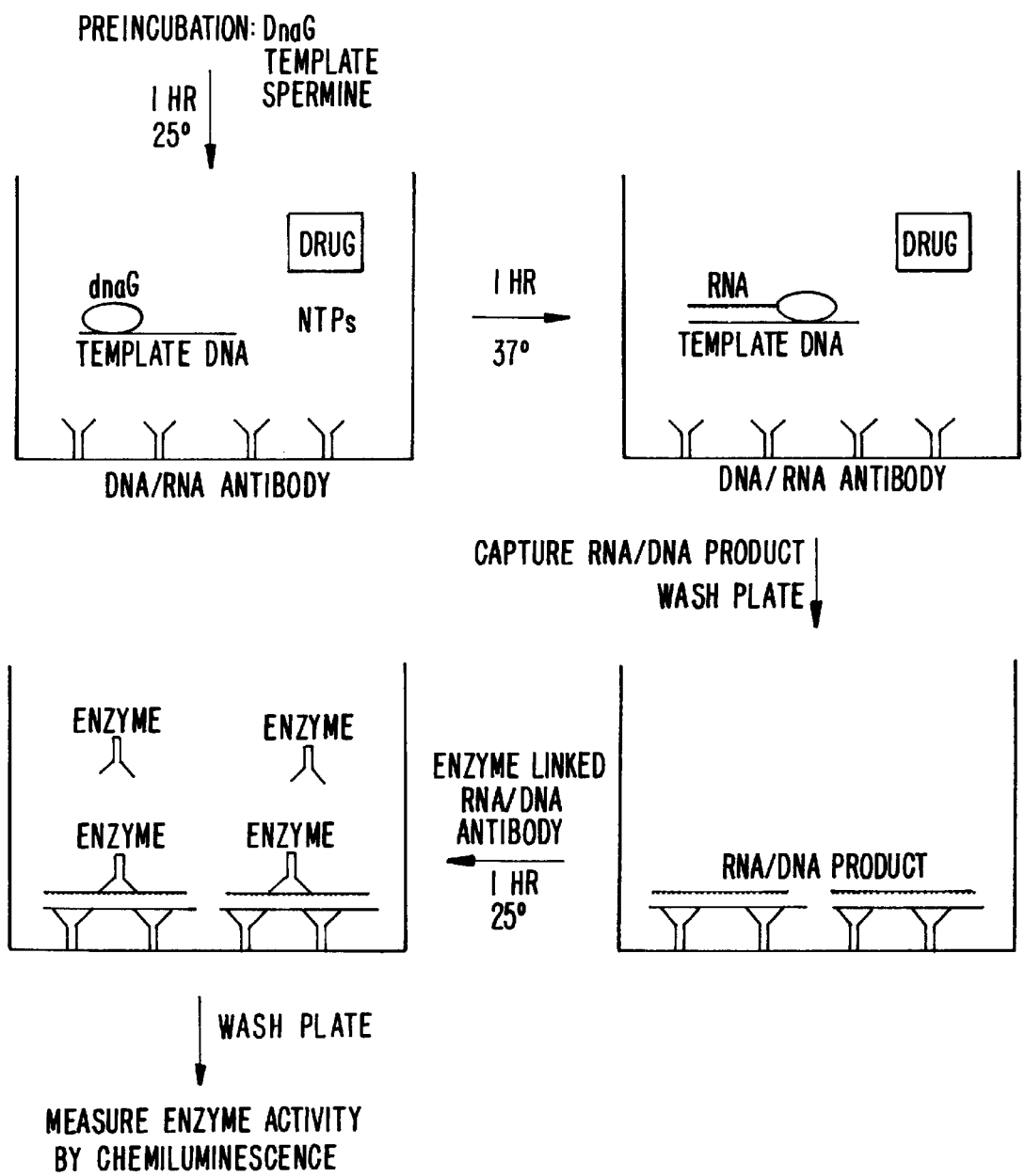
FIG. 1 shows a schematic diagram of a solution-phase chemiluminescence assay for DnaG primase activity. The DnaG primase, a template DNA, and spermine are preincubated at 25° C. for one hour. The preincubated components are then added to a microtiter well which is coated with antibodies that bind DNA-RNA heteroduplexes. The microtiter well also includes a potential modulator of primase activity ("drug") and the four ribonucleotides. The mixture is incubated for one hour at 37° C., during which time the primase synthesizes an RNA primer unless the potential activity modulator blocks primase activity. The resulting DNA-RNA heterohybrid regions are captured by the heteroduplex-specific antibodies. After the plate is washed, an enzyme-linked antibody that binds to DNA-RNA heterohybrid regions is added to the well and incubated for one hour at 25° C. The plate is again washed, and bound enzyme activity is measured by chemiluminescence.

The following terms are expressly defined for purposes of this application.

A "ribonucleic acid" or "RNA" is a polymer comprising ribonucleotide monomer units. The polymer can be a naturally occurring ribonucleotide polymer such as mRNA, rRNA or tRNA. The polymer optionally comprises non-naturally occurring nucleotides, e.g., synthetic monomer units in the polymer chain. The RNA can be single or double stranded. A "region" of the RNA is any sequence or subsequence of the RNA, including the full-length of the RNA.

An "RNA duplex" is a double stranded nucleic acid comprising at least one RNA strand. The duplex can be RNA:RNA, RNA:DNA (also referred to as an DNA:RNA hybrid or DNA:RNA heteroduplex) or can comprise artificial nucleotides. An RNA homoduplex is a base-paired double-stranded RNA. An RNA heteroduplex comprises an RNA strand and a strand comprising DNA nucleotide monomers. All or a region of the duplex may be double stranded. Typically, at least 10 bases of the duplex will be double-stranded.

A "recognition reagent" is a reagent that is directly or indirectly detectable and that binds, directly or indirectly, to the indicated molecule (e.g., RNA duplex, homoduplex or heteroduplex). A typical recognition reagent in the context of the invention is an antibody that specifically binds nucleic acid duplexes or an oligonucleotide that specifically hybridizes to a selected RNA. Optionally, the recognition reagent is immobilized on a solid support.

A "detectable moiety" or "label" is a composition that is detectable, either directly or indirectly, by spectroscopic, photochemical, biochemical, immunochemical, or chemical means. For example, useful labels include $^{32}P$, fluorescent dyes, electron-dense reagents, enzymes and their substrates (e.g., as commonly used in enzyme-linked immunoassays, e.g., alkaline phosphatase and horse radish peroxidase), biotin-streptavidin, digoxigenin, or haptens and proteins for which antisera or monoclonal antibodies are available. The label or detectable moiety is typically bound, either covalently, through a linker or chemical bound, or through ionic, van der Waals or hydrogen bonds to the molecule to be detected.

A "modulator of primase activity" is a compound that increases or decreases synthesis of an RNA oligonucleotide on a DNA template in a selected system. A "potential modulator of primase activity" is a compound that is to be assessed for the ability to increase or decrease synthesis of an RNA oligonucleotide on a DNA template in a selected system. Samples or assays that are treated with a potential modulator are compared to control samples without the test compound, to examine the extent of inhibition or activation of primase activity. Control samples (untreated with test inhibitors or activators) are assigned a relative primase activity value of 100. Inhibition of primase activity is achieved when the primase activity value of the test sample relative to the control is about 75, preferably 50, more preferably 25. Activation is achieved when the primase activity value of the test sample relative to the control is about 150, more preferably 200.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

The phrase "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

Description of the Preferred Embodiments

The present invention provides methods for measuring the activity of nucleic acid primases, and methods for identifying modulators of primase activity. The methods are efficient and readily amenable to high-throughput drug screening protocols, as gel separation steps are avoided. High-throughput screening (HTS) methods, compositions, kits and integrated systems for performing the assays are also provided. In general, the assays are performed by incubating a reaction mixture that contains a primase, a DNA template for the primase, and ribonucleotide triphosphates under conditions such that the primase can polymerase the ribonucleotide triphosphates on the template to form a nucleic acid that has one or more DNA-RNA heterohybrid regions.

The assays of the invention provide two approaches by which high efficiency is achieved. In the first approach, the nucleic acid is contacted with a recognition reagent that specifically binds to a DNA-RNA heterohybrid region. The recognition reagent also includes a tag that can bind to a solid support. Binding of the tag to a solid support thus results in immobilization of DNA-RNA heterohybrid regions. The presence or absence of immobilized regions on the solid support is then detected. In an alternative embodiment, the DNA template is immobilized on a solid support. The immobilized DNA template is contacted with a reaction mixture that includes a primase and ribonucleotide triphosphates, and the reaction mixture is incubated under conditions in which the primase can polymerize the triphosphates on the template to form a nucleic acid that includes one or more DNA-RNA heterohybrid regions. The presence or absence of DNA-RNA heterohybrid regions bound to the solid support is then detected.

The invention represents an improvement over existing technology for assaying primase activity in several ways. For example, (a) previously available assays generally required isolation of the primer, a difficult task due to the short length of the primer and the small amount of primer present in a cell compared to the total amount of nucleic acid; (b) the assays are highly sensitive, allowing detection of 100–200 attomoles of primer; (c) the assays of the invention do not require the use of radioactive reagents (although they are optionally used as discussed below); (d) gel separations steps are entirely avoided; (e) each of the formats described is fast and readily amenable for automation and high throughput screening ("HTS") using current reagents, devices and methodologies. The method steps can be repeated in parallel in a microtiter plate format, for example, thus allowing one to screen at least about 1,000 different potential activity modulators for an effect on primase activity in a single day.

Primase modulators identified by use of the assays of the invention have value for in vitro modification of primase activity, e.g., as tools for recombinant methods, cell culture modulators, and the like. More importantly, these modulators provide lead compounds for drug development for a variety of conditions, including antibacterial, antifungal, antiviral or antineoplastic agents. Accordingly, the assays are of immediate value for their ability to identify lead compounds for pharmaceutical or other applications.

Indeed, because primases play a central role in nucleic acid metabolism and thus are important in a variety of biological processes relating to cell division and DNA replication, primase activity modulators identified by the assays of the invention are leads for a variety of conditions, including neoplasia, viral infection, bacterial infection, fungal infection, and the like. In addition, primase modulators which specifically target undesired organisms, such as viruses, fungi, agricultural pests, or the like, can serve as fungicides, bactericides, herbicides, insecticides, and the like. Thus, the range of conditions that primase activity modulators are applicable to includes conditions in humans and other animals, and in plants, e.g., for agricultural applications.

Primases

The assay methods of the invention are useful for measuring the activities, and for identifying inhibitors of, any of the numerous types of primases. Primases are capable of synthesizing relatively short (typically 7–11 nucleotide) RNA primers using DNA as a template. Unlike RNA polymerases, primases are generally insensitive to relatively high concentrations of antibiotics such as rifampicin, α-amanitin, and actinomycin D. Also unlike RNA polymerases, primers do not require a promoter region adjacent to the site of initiation of RNA synthesis.

Three families of primases are currently known: primases of bacteria and bacteriophage, primases of eukaryotes, and primases of eukaryotic viruses. Most primases share several features, including 1) an Asp-Xxx-Asp motif that is characteristic of polymerases, 2) a zinc-binding motif, and 3) an RNAP motif. The bacterial primases and some of the bacteriophage primases are typically active as monomers. Many bacterial primase nucleotide and amino acid sequences are known, including *Bacillus subtilis* (X03897), *Clostridium acetobutylicum* (Z23080), *Escherichia coli* (J01687), *Haemophilus influenzae* (L11044), *Helicobacter pylori* (AE000523), *Lactococcus lactis* (D10168), *Legionella pneumophila* (U63641), *Listeria monocytogenes* (U13165), *Myxococcus xanthus* (U20669), *Mycoplasm genitalium* (U39703), *Mycoplasma pneumoniae* (1674174), *Mycobacterium tuberculosis* (Z83860), *Pseudomonas putida* (U85774), *Rickettsia prowazekii* (M95860), *Salmonella typhimurium* (M14427), *Staphylococcus aureus* (AB001896), Synechococcus PCC7942, *Cyanobacteria chroococcales* (X94247), *Synechocystis sp., Cyanobacteria chroococcales* (D90912). Bacteriophage primases for which nucleotide and amino acid sequences are known include, for example, T7 (gene 4 protein), T3 (gene 4 protein), P4 (α protein) and T4 (gene 41 protein).

Eukaryotic primase activity is typically associated with two types of multimeric complex. Primases involved in DNA replication are generally found in a complex with DNA polymerase α; these complexes typically include two primase subunits (Pri1 (49 kDa) and Pri2 (58 kDa)), as well as DNA polymerase α and a p70–90 subunit. Primase activity is also found as a heterodimer which consists of the Pri1 and Pri2 subunits. The active site for RNA polymer elongation is found in the Pri1 subunit, while initiation generally involves the Pri2 subunit. Amino acid and nucleotide sequences for several eukaryotic primase Pri1 subunits have been characterized, including human (Swissprot Accession No. P49642, Genbank X74330), *Mus musculus* (GenBank J04620), *Rattus norvegicus* PID:g1763025, *Drosophila melanogaster* p50 (PID:g666989), *Caenorhabditis elegans* p48 (SP:P34471), *Saccharomyces cerevisiae* p48 (SP:P10363), *Schizosaccharomyces pombe* p53 (Acc# Z98531:22398 . . . 23846), *Plasmodium falciparum* p53 (Acc# X99254:486 . . . 3750). Archaeobacteria having primases that are similar to the eukaryotic Pri1 include *Methanococcus jannaschii* (Acc# Q58249), *Archaeoglobus fulgidus* (Acc# AE001054:8352 . . . 9434), and *Methanobacterium thermoautotrophicum* (Acc# AE000840:7684 . . . 8655). Pri2 primases have been sequenced from human Acc# P49643, *Mus musculus* Acc# S45629, *Caenorhabditis elegans* (Acc# Z81137) *Saccharomyces cerevisiae* (Acc# P20457) and the plant *Arabidopsis thalians* (Acc# AC002130:39565 . . . 46348).

When assaying for inhibitors of primase activity, preferred primases are typically selected from medically relevant sources such as HSV1, HSV2, helicase/primase complex (UL5/8/52), a related primase from CMV, DnaG from bacteria (e.g., for assays designed to identify compounds which modulate cell growth, e.g., for inhibition of neoplasia); or from infectious organisms such as infectious fungi, e.g., Aspergillus, Candidaspecies; bacteria, particularly *E. coli*, which serves a model for pathogenic bacteria, as well as medically important bacteria such as Staphylococci (e.g., *aureus*), Streptococci (e.g. *pneumoniae*), Clostridia (e.g., *perfringens*), Neisseria (e.g., *gonorrhoea*), Enterobacteriaceae (e.g., *coli*), Helicobacter (e.g., *pylori*), Vibrio (e.g., *cholerae*), Capylobacter (e.g., *jejuni*), Pseudomonas (e.g., *aeruginosa*), Haemophilus (e.g., *influenzae*), Bordetella (e.g., *pertussis*), Mycoplasma (e.g., *pneumoniae*), Ureaplasma (e.g., *urealyticum*), Legionella (e.g., *pneumophila*), Spirochetes (e.g., Treponema, Leptospira and Borrelia), Mycobacteria (e.g., *tuberculosis, smegmatis*), Actinomyces (e.g., *israelii*), Nocardia (e.g., *asteroides*), Chlamydia (e.g., *trachomatis*), Rickettsia, Coxiella, Ehrlichia, Rochalimaea, Brucella, Yersinia, Fracisella, and Pasteurella; protozoa such as sporozoa (e.g., Plasmodia), rhizopods (e.g., Entamoeba) and flagellates (Trypanosoma, Leishmania, Trichomonas Giardia, etc.); viruses such as the (+) RNA Poxviruses (e.g., *vaccinia*) viruses and certain dsDNA viruses (e.g., African Swine Fever Virus). Other assays are designed to be relevant to non-medical uses, such as assays for inhibitors of primases from crop pests e.g., insects, fungi, weed plants, and the like.

Primases to be used in the assays of the invention can be purified from a natural source or may be recombinantly produced, and are usually provided in at least a partially-purified form, although the assays can function when provided with a crude cell lysate that contains a primase. In a preferred embodiment, the primases are synthesized using recombinant DNA methodology. Generally this involves creating a DNA sequence that encodes the primase, modified as desired, placing the DNA in an expression cassette under the control of a particular promoter, expressing the protein in a host, isolating the expressed protein and, if required, renaturing the protein. Primase nucleic acids that are useful for recombinant production of primases for use in the assays of the invention, and methods of obtaining such nucleic acids, are known to those of skill in the art. Primase nucleic acids (e.g., cDNA, genomic, or subsequences (probes)) can be cloned, or amplified by in vitro methods such as the polymerase chain reaction (PCR), the ligase chain reaction (LCR), the transcription-based amplification system (TAS), the self-sustained sequence replication system (SSR). A wide variety of cloning and in vitro amplification methodologies are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, NY, (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864. Examples of techniques sufficient to direct persons of skill through in vitro amplification methods are found in Berger, Sambrook, and Ausubel, as well as Mullis et al. (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Research* (1991) 3: 81–94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.*, 35: 1826; Landegren et al., (1988) *Science*, 241: 1077–1080; Van Brunt (1990) *Biotechnology*, 8: 291–294; Wu and Wallace, (1989) *Gene*, 4: 560; and Barringer et al. (1990) *Gene*, 89: 117.

DNA encoding the primases can be prepared by any suitable method as described above, including, for example, cloning and restriction of appropriate sequences or direct chemical synthesis by methods such as the phosphotriester method of Narang et al. (1979) *Meth. Enzymol.* 68: 90–99; the phosphodiester method of Brown et al. (1979) *Meth. Enzymol.* 68: 109–151; the diethylphosphoramidite method of Beaucage et al. (1981) *Tetra. Lett.*, 22: 1859–1862; and the solid support method of U.S. Pat. No. 4,458,066. In one preferred embodiment, a nucleic acid encoding a primase can be isolated by routine cloning methods. A nucleotide sequence of a primase gene as provided in, for example, GenBank or other sequence database can be used to provide probes that specifically hybridize to a primase gene in a genomic DNA sample, or to a primase mRNA in a total RNA sample (e.g., in a Southern or Northern blot). Once the target primase nucleic acid is identified, it can be isolated according to standard methods known to those of skill in the art (see, e.g., Sambrook et al. (1989) *Molecular Cloning: A Laboratory Manual*, 2nd Ed., Vols. 1–3, Cold Spring Harbor Laboratory; Berger and Kimmel (1987) *Methods in Enzymology*, Vol. 152: *Guide to Molecular Cloning Techniques*, San Diego: Academic Press, Inc.; or Ausubel et al. (1987) *Current Protocols in Molecular Biology*, Greene Publishing and Wiley-Interscience, New York).

Primases can be expressed in a variety of host cells, including *E. coli*, other bacterial hosts, yeast, and various higher eukaryotic cells such as the COS, CHO and HeLa cells lines and myeloma cell lines. Examples of useful bacteria include, but are not limited to, Escherichia, Enterobacter, Azotobacter, Erwinia, Bacillus, Pseudomonas, Klebsielia, Proteus, Salmonella, Serratia, Shigella, Rhizobia, Vitreoscilla, and Paracoccus. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids encoding primases can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant primases can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol. 182: Guide to Protein Purification.*, Academic Press, Inc. N.Y. (1990)). Substantially pure compositions of at least about 90 to 95% homogeneity are preferred, and 98 to 99% or more homogeneity are most preferred. Once purified, partially or to homogeneity as desired, the polypeptides may then be used (e.g., as immunogens for antibody production).

Occasionally only a portion of a native primase is used in the assay, the portion being sufficient for primase activity of preferably not less than an order of magnitude less than that of the full-length primase. Portions capable of imparting the requisite binding specificity and affinity are readily identified by those skilled in the art. A wide variety of molecular and biochemical methods are available for generating catalytic fragments of a primase.

Primase Reaction Mixtures

The primase assays are carried out in mixtures that include, in addition to a primase, a nucleic acid template and ribonucleotide triphosphates under conditions in which the primase is catalytically active. A wide variety of incubation conditions can be used, depending on the primase of interest. Reaction conditions in which various primases are active in vitro are exemplified below and/or are otherwise known in the art. For many primases that are found in mammals, either native to the animal or as a result of infection by a pathogen, the reaction is carried out at room temperature or slightly greater, usually in the range of 20–40° C. Primases are active across a relatively broad pH range, preferably between about 6–8. Reactions can also include one or more of $Mg^{2+}$, glycerol, a reducing agent (e.g., 2–5 mM dithiothreitol), a condensing agent (e.g., 5 mM spermidine), and an inert enzyme stabilizer (e.g., BSA). For high throughput applications, the reaction time is minimized. Typically, the reaction is carried out for between 0.1 and 4 hours, more typically between about 0.5 and 1.5 hours.

The nucleic acid template used in the primase assays of the invention can be linear or circular, depending on source convenience and the specificity of the targeted primase. While DNA is the preferred template material, other nucleic acids or structural analogs may be substituted so long as they provide an active substrate for the targeted primase activity. The nucleic acids can be of any length sufficient to provide a substrate for the primase, a template for assay-detectable nascent primer(s), and that is otherwise amenable to the assay conditions and requirements. The template is typically at least about 20 bp, preferably at least about 40 bp in length; however, for embodiments providing a multiple of discrete regions, the template is typically one or more kb in length, with optimal lengths readily determined empirically. The template may be of any sequence which provides a substrate to which the targeted primase(s) can bind. The most convenient and inexpensive sources of template DNA depend on the substrate specificities of the targeted primase. Substrate specificities for some primases are known in the art or are readily determined empirically. The most cost-effective DNA sources are often sufficient for detecting a given primase activity, e.g., alkaline denatured DNA extracts from salmon sperm, calf thymus, replicated vectors and plasmids, such as, for example, M13, φX174, ColE1 plasmids such as PBR322 and derivatives, etc., single-stranded sources such as synthetic polynucleotides, ssM13, ssφX174, etc. A panel and/or variety of potential template substrates, e.g. DNA(s) of varied size, sequence, protein complexing, etc. can be provided to improve the likelihood of detecting substrate-sensitive primases.

The DNA templates used in the assay methods of the invention need not include a promoter region. Primases can synthesize RNA primers even in regions that are not adjacent to promoter regions on the templates. In preferred embodiments, the primases initiate synthesis of the primers at least about 10 nucleotides distant from the nearest upstream promoter region in the template, more preferably at least about 50 nucleotides distant, and most preferably at least about 100 nucleotides distant from the nearest upstream promoter region.

The mixture also comprises ribose nucleotide triphosphates or analogs thereof, preferably an approximately equimolar mixture of ATP, CTP, GTP and UTP for a template that includes all for corresponding deoxynucleotides. Of course, where the template includes less than all deoxynucleotides, the reaction mixture need not include ribonucleotides that correspond to the deoxynucleotides not found in the template. In some embodiments, at least one of the triphosphates is a nucleotide derivative and/or comprises a detectable label. In addition, the mixture usually includes additional reagents, such as salts, buffers, etc., to facilitate or maximize primase activity. Also, reagents that reduce non-specific or background activity or otherwise improve the efficiency of the assay, such as protease inhibitors, nuclease inhibitors, spermine, antimicrobial agents, etc. may be used.

For some primase assays, it is desirable to include in the reaction mixture deoxynucleotide triphosphates in addition to the ribonucleotide triphosphates that are polymerized by the primase. For example, where the primase being assayed is present as a complex with DNA polymerase α, the inclusion of deoxynucleotide triphosphates in the reaction mixture can increase the amount of DNA-RNA heterohybrid regions formed by the primase (see, e.g., Sheaff et al. (1994) *Biochemistry* 33: 2247–2254).

The RNA primers synthesized by primase enzymes are typically about 2–10 nucleotides in length, most commonly about 7–10 nucleotides, although longer primers are sometimes made. Depending on the particular template employed in an assay, one or many primers can be synthesized on a template molecule. Generally, at least about five, preferably at least about ten, more preferably at least about twenty, and most preferably at least about thirty regions are synthesized on a template molecule during the course of the primase reaction.

Primase Assay Formats

The invention provides two basic primase assay formats. In the first method, the DNA template is in solution during the primase-catalyzed polymerization reaction. DNA-RNA hybrids that result from primase activity are then detected, preferably after being immobilized. The second assay method involves carrying out the primase reaction using a pre-immobilized DNA template.

Solution Phase Assays.

The solution phase assays of the invention involve carrying out the primase reaction on a nucleic acid template that is in solution. A reaction mixture of a primase, a suitable template, and ribonucleotide triphosphates is incubated under conditions in which the primase polymerizes the triphosphates on the template to form a nucleic acid that has one or more DNA-RNA heterohybrid regions.

In preferred embodiments of the solution phase assays, the nucleic acids that include DNA-RNA heterohybrid regions are immobilized, either directly or indirectly, on a solid support such as a bead, a membrane, or a plate by non-covalent attachment to the support under suitable buffer conditions. For example, a recognition reagent such as those discussed in detail below, e.g., an antibody that recognizes RNA:DNA heteroduplexes, or a non-catalytically active RNAse H mutant, can be immobilized on a plate, thereby capturing DNA-RNA heterohybrid regions. The recognition reagent can be pre-immobilized on the solid support prior to the primase reaction, or can become immobilized during or after the course of the reaction. The recognition reagents are typically bifunctional, having a first binding moiety specific for the nucleic acid and a second moiety specific for the substrate or a functional group bound to the substrate. The recognition reagent used in the solution phase assays of the invention can include a tag that mediates binding of the recognition reagent to the solid support. The tag can be any of a variety of components. In general, a molecule which binds the tag (a tag binder) is fixed to a solid support, and the tagged recognition reagent is attached to the solid support by interaction of the tag and the tag binder. A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Antibodies to molecules with natural binders such as biotin are also widely available and appropriate tag binders; see, SIGMA Immunochemicals 1998 catalogue SIGMA, St. Louis, Mo.).

Similarly, any haptenic or antigenic compound can be used in combination with an appropriate antibody to form a tag/tag binder pair. Thousands of specific antibodies are commercially available and many additional antibodies are described in the literature. See, id. Indeed, the antibody can be either the tag or the tag binder, or antibodies can be used as both tags and tag binders. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as e.g., transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott and Power (1993) *The Adhesion Molecule FactsBook*, Academic Press New York, and Hulme (ed) *Receptor Ligand Interactions A Practical Approach*, Rickwood and Hames (series editors) Hulme (ed) IRL Press at Oxford Press NY).

Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers such as heteropolymers in which a known drug is covalently bound to any of the above, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Specific tag-tag binder interactions occur when the tag and tag binder bind with a $K_D$ of at least about 0.01 μM, preferably at least about 0.001 μM or better, and most typically and preferably, 0.0001 μM or better, under standard assay conditions.

Methods for the attachment of tags to reagents that bind to DNA-RNA heterohybrid regions are known to those of skill in the art. Where the moiety that binds a DNA-RNA heterohybrid region is a polypeptide, a preferred embodiment of preparing a recognition reagent involves producing a fusion protein by recombinant methods. For example, a polynucleotide encoding the DNA-RNA heterohybrid region binding moiety is operably linked to a polynucleotide that encodes an epitope for which convenient means of detection exist. The polynucleotide encoding the epitope is preferably placed at a location relative to the binding moiety coding sequence that does not disrupt the ability of the fusion protein to bind DNA-RNA heterohybrid regions. Methods for constructing and expressing genes that encode fusion proteins are well known to those of skill in the art. Examples of these techniques and instructions sufficient to direct persons of skill through many cloning exercises are found in Berger, Sambrook, and Ausubel, supra. Examples of suitable epitopes include the myc and V-5 reporter genes; expression vectors useful for recombinant production of recognition reagents having these epitopes are commercially available (e.g., Invitrogen (Carlsbad, Calif.) vectors pcDNA3.1/Myc-His and pcDNA3.1/V5-His are suitable for expression in mammalian cells). Additional expression vectors for suitable fusion proteins, and corresponding detection systems are known to those of skill in the art, and several are commercially available (e.g., FLAG™ (Kodak, Rochester, N.Y.). Another example of a suitable tag is a polyhistidine sequence, which is capable of binding to metal chelate affinity ligands. Typically, six adjacent histidines are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In *Genetic Engineering: Principles and Methods*, J. K. Setlow, Ed., Plenum Press, NY; commercially available from Qiagen (Santa Clarita, Calif.)).

Other haptens that are suitable for use as tags are known to those of skill in the art and are described, for example, in the *Handbook of Fluorescent Probes and Research Chemicals* (6th Ed., Molecular Probes, Inc., Eugene, Oreg.). For example, dinitrophenol (DNP), digoxigenin, barbiturates (see, e.g., U.S. Pat. No. 5,414,085), and several types of fluorophores are useful as haptens, as are derivatives of these compounds. Kits are commercially available for linking haptens and other moieties to proteins and other molecules. For example, the hapten includes a thiol, a heterobifunctional linker such as SMCC can be used to attach the tag to lysine residues present on the recognition moiety.

Tag binders are fixed to solid substrates using any of a variety of methods currently available. Solid substrates are commonly derivitized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield (1963) *J. Am. Chem. Soc*. 85: 2149–2154 (describing solid phase synthesis of, e.g., peptides); Geysen et al. (1987) *J. Immun. Meth*. 102: 259–274 (describing synthesis of solid phase components on pins). See, Frank and Doring (1988) *Tetrahedron* 44: 6031–6040 (describing synthesis of various peptide sequences on cellulose disks); Fodor et al. (1991) *Science* 251: 767–777; Sheldon et al. (1993) *Clinical Chemistry* 39(4): 718–719 and Kozal et al. (1996) *Nature Medicine* 2(7): 753–759 (all describing arrays of biopolymers fixed to solid substrates). Non-chemical approaches for fixing tag binders to substrates include other common methods, such as heat, cross-linking by UV radiation, and the like.

The tag can also be incorporated directly into the RNA primer synthesized by the primase. For example, the reaction mixture can include one or more ribonucleotides that are conjugated to a molecule such as a biotin moiety, which has the ability to bind a second molecule, e.g., a streptavidin molecule, that is bound to a solid support. Such ribonucleotides would be incorporated into the primase-synthesized RNA primer.

Solid supports suitable for use in the primase assays of the invention are known to those of skill in the art. As used herein, a solid support is a matrix of material in a substantially fixed arrangement. Exemplar solid supports include glasses, plastics, polymers, metals, metalloids, ceramics, organics, etc. Solid supports can be flat or planar, or can have substantially different conformations. For example, the substrate can exist as particles, beads, strands, precipitates, gels, sheets, tubing, spheres, containers, capillaries, pads, slices, films, plates, slides, etc. Magnetic beads or particles, such as magnetic latex beads and iron oxide particles, are examples of solid substrates that can be used in the methods of the invention. Magnetic particles are described in, for example, U.S. Pat. No. 4,672,040, and are commercially available from, for example, PerSeptive Biosystems, Inc. (Framingham, Mass.), Ciba Corning (Medfield, Mass.), Bangs Laboratories (Carmel, Ind.), and BioQuest, Inc. (Atkinson, N.H.).

Solid Phase Assays.

In the solid phase assays of the invention, the nucleic acid template is immobilized prior to exposure to the primase enzyme. This method thus is advantageous over other methods in that the newly synthesized primer need not be subjected to purification steps after synthesis.

Attachment of DNA or RNA nucleic acids to various solid supports is performed using available techniques. For example, one can attach to the nucleic acid a tag which has an affinity to a derivatized solid support. Suitable tags and corresponding tag binders are discussed above. In one embodiment, linkers are added to the nucleic acid and attachment to the tag is performed through the linker. Common linkers include polypeptide sequences, such as poly gly sequences of between about 5 and 200 amino acids. In some embodiments, proline residues are incorporated into the linker to prevent the formation of significant secondary structural elements by the linker. Such flexible linkers are known to persons of skill in the art. For example, poly (ethylene glycol) linkers are available from Shearwater Polymers, Inc., Huntsville, Ala. These linkers optionally have amide linkages, sulfhydryl linkages, or heterofunctional linkages. Solid supports which have suitable derivatives for immobilization of DNA are commercially available (e.g., DNA-Bind plates, Costar).

Similarly, the tagged nucleic acid may be directly attached to a solid substrate in the assays of the invention. In this embodiment, the terminal end of the tagged nucleic acid is, itself, the molecular tag. In this embodiment, tagged nucleic acids are fixed to or synthesized on a solid support. For example, using chip masking technologies and photoprotective chemistry it is possible to generate arrays of nucleic acid probes. These arrays, which are known, e.g., as "DNA chips," can include millions of nucleic acid regions on a substrate having an area of about 1 cm$^2$ to several cm$^2$, thereby incorporating sets of from a few to millions of tagged nucleic acids. See, e.g., Fodor et al. (1991) *Science*, 251: 767–777; Sheldon et al. (1993) *Clinical Chemistry* 39(4): 718–719, and Kozal et al. (1996) *Nature Medicine* 2(7): 753–759.

The immobilized template nucleic acid is contacted with a reaction mixture such as is described above that includes the primase and ribonucleotide triphosphates. If active primase is present in the reaction mixture, a nucleic acid is formed which includes DNA-RNA heterohybrid regions. The presence or absence of such regions immobilized on the solid support is then detected. The primase reactions are as described above.

Recognition Reagents for DNA:RNA Hybrids

The assay methods of the invention involve binding of an agent to DNA-RNA heterohybrid regions that result from primase activity, for purposes of immobilization (in the solution phase assays) and/or labeling (both solution phase and solid phase assays). Several methods of achieving specific binding to a DNA-RNA heterohybrid region are available.

In one embodiment, recognition of DNA-RNA heterohybrid regions is achieved by incorporating into the primase-synthesized RNA strand one or more ribonucleotides that are derivatized with a hapten for which specific binding agents are available. For example, the reaction mixture can include one or more ribonucleotides that are derivatized a chemical group that has a specific affinity for a particular recognition reagent. The particular derivatized ribonucleotides used in this application should be capable of incorporation into an RNA strand by the primase enzyme. Examples of suitable chemical groups include, but are not limited to, biotin, digoxigenin, and other haptens or proteins for which suitable binding partners, e.g., antisera or monoclonal antibodies are available.

Most commonly, the recognition reagent will be an antibody which recognizes DNA-RNA heterohybrid regions. Coutlee et al. (1989) *Analytical Biochemistry* 181:153–162; Bogulavski et al. (1986) *J. Immunol. Methods* 89:123–130; Prooijen-Knegt (1982) *Exp. Cell Res.* 141:397–407; Rudkin (1976) *Nature* 265:472–473, Stollar (1970) *PNAS* 65:993–1000; Ballard (1982) *Mol. Immunol.* 19:793–799; Pisetsky and Caster (1982) *Mol. Immunol.* 19:645–650; Viscidi et al. (1988) *J. Clin. Microbial.* 41:199–209, and Kiney et al. (1989) *J. Clin. Microbiol.* 27:6–12 describe antibodies to RNA duplexes, including homo and heteroduplexes. Kits comprising antibodies specific for DNA:RNA hybrids are available, e.g., from Digene Diagnostics, Inc. (Beltsville, Md.). Accordingly, such antibodies are commercially available.

In addition to available antibodies, one of skill can easily make antibodies specific for DNA-RNA heterohybrid regions using existing techniques, or modify those antibodies which are commercially or publicly available. In addition to the art referenced above, general methods of producing polyclonal and monoclonal antibodies are known to those of skill in the art. See, e.g., Paul (ed) (1993) *Fundamental Immunology, Third Edition* Raven Press, Ltd., New York Coligan (1991) *Current Protocols in Immunology* Wiley/Greene, NY; Harlow and Lane (1989) *Antibodies: A Laboratory Manual* Cold Spring Harbor Press, NY; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) *Nature* 256: 495–497. Other suitable techniques for antibody preparation include selection of libraries of recombinant antibodies in phage or similar vectors. See, Huse et al. (1989) *Science* 246: 1275–1281; and Ward et al. (1989) *Nature* 341: 544–546. Specific monoclonal and polyclonal antibodies and antisera will usually bind with a $K_D$ of at least about 0.1 $\mu$M, preferably at least about 0.01 $\mu$M or better, and most typically and preferably, 0.001 $\mu$M or better.

As used herein, an "antibody" refers to a protein consisting of one or more polypeptide substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region thereby converting the (Fab')$_2$ dimer into an Fab' monomer. The Fab' monomer is essentially an Fab with part of the hinge region (see, *Fundamental Immunology*, W. E. Paul, ed., Raven Press, NY (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Antibodies include single chain antibodies, including single chain Fv (sFv) antibodies in which a variable heavy and a variable light chain are joined together (directly or through a peptide linker) to form a continuous polypeptide.

Indeed, the DNA-RNA heterohybrid region binding site from an antibody can be fused by recombinant methods to non-immunoglobulin protein sequences to form a recognition reagent which binds to a DNA-RNA heterohybrid region. An "DNA-RNA heterohybrid region binding site" or "binding portion" with reference to an antibody or antibody fusion molecule refers to the part of an immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target RNA. The three hypervariable regions of each of the heavy and light chains are referred to as "complementarity determining regions" or "CDRs" and are characterized, for example by Kabat et al. *Sequences of proteins of immunological interest*, 4th ed. U.S. Dept. Health and Human Services, Public Health Services, Bethesda, Md. (1987).

As used herein, the terms "immunological binding" and "immunological binding properties" refer to the non-covalent interactions of the type which occur between a recognition reagent and a DNA-RNA heterohybrid region for which the reagent is specific. The strength or affinity of binding interactions can be expressed in terms of the dissociation constant ($K_d$) of the interaction, wherein a smaller $K_d$ represents a greater affinity. Binding properties of selected reagents can be quantified using methods well known in the art. One such method entails measuring the rates of DNA-RNA heterohybrid region-recognition reagent complex formation and dissociation, wherein those rates depend on the concentrations of the complex partners, the affinity of the interaction, and on parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity and is thus equal to the dissociation constant $K_d$. See, generally, Davies et al. (1990) *Ann. Rev. Biochem.*, 59: 439–473.

It will be appreciated that molecules other than immunoglobulins and derivatives also make appropriate recognition reagents, and can be made by one of skill. In general, molecules which recognize DNA-RNA heterohybrid regions (and which, preferably, do not recognize DNA homoduplexes) are suitable. Molecules which bind DNA-RNA heterohybrid regions include antibodies, nucleic acid binding proteins, nucleic acids and the like. One example of a suitable moiety that specifically binds DNA-RNA heterohybrid regions and thus is suitable for use in a recognition reagent is an RNAse H polypeptide that has been mutated so as to lack catalytic activity. Active RNAse H degrades the RNA moiety of DNA-RNA heteroduplexes; thus by disrupting the catalytic activity but maintaining the binding specificity for DNA-RNA heterohybrids, one can obtain a polypeptide that is useful as a recognition reagent in the assays of the invention. Additional appropriate reagents can be identified, e.g., by screening available combinatorial chemical (e.g., peptide) libraries to find library members which preferentially bind DNA-RNA heterohybrid regions.

As described, recognition reagents of the invention are optionally made via recombinant ligation of nucleic acids encoding the constituent parts of the encoded fusion protein (e.g., RNA recognition domain, linker and a label such as a phosphatase, peroxidase or other enzyme) and expression of the resulting construct. Instructions sufficient to direct one of skill through such cloning exercises are found in Sambrook, Berger and Ausubel, all supra, and again, many appropriate recognition reagents, including reagents comprising label domains, are available.

Detection of DNA-RNA Heterohybrid Regions

Following the primase reaction, the solid substrate upon which is immobilized any nucleic acids that include DNA-RNA heterohybrid regions synthesized by the primase is typically washed free of unbound components. The method used for separating and washing depends on the nature of the reaction reservoir and the solid substrate. For example, where the substrate is in the form of aggregated fibers, the solid phase can be physically transferred from the reaction reservoir to a series of rinse reservoirs; for beads, the separating and washing steps are typically performed by filtration, frequently vacuum-assisted filtration; and for plates, rinsing or flooding and aspirating or decanting are effective.

The amount of primase activity is then inferred from the amount of immobilized DNA-RNA heterohybrid region, which can be measured in a variety of ways. For example, one or more of the ribose nucleotide triphosphates may comprise a directly and/or indirectly detectable label which is then incorporated into the heterohybrid regions. Exemplary labels include epitope tags, radiolabels, biotin, derivatized nucleotides such as digoxigenin, etc. The label may provide a directly detected signal or may be detected indirectly, for example, with label-specific receptors such as antibodies. In particular, directly and/or indirectly detectable receptors specific for the label may be used to provide or amplify the signal provided by the label.

Alternatively, one can employ a recognition reagent that is directly or indirectly detectable. Where a recognition reagent is used for immobilization of the nucleic acids that include DNA-RNA heterohybrid regions, e.g., in the solution phase assays, a second recognition reagent is used for detection. In such assays, the first recognition reagent, which is used for immobilization, can be, for example, an anti-RNA:DNA antibody labeled with biotin, which binds to a streptavidin-coated solid support. The second recognition reagent, which is used for detection and is also referred to herein as a "detection reagent," can be, for example an anti-RNA:DNA antibody conjugated to an alkaline phosphatase enzyme or other label that is detectable either directly or indirectly.

The detection reagents are either directly labeled, i.e., comprise or react to produce a detectable label, or are indirectly labeled, i.e., bind to a molecule comprising or reacting to produce a detectable label. Labels can be directly attached to or incorporated into the detection reagent by chemical or recombinant methods.

In one embodiment, a label is coupled to a molecule, such as an antibody comprising the DNA-RNA heterohybrid region recognition domain, through a chemical linker. Linker domains are typically polypeptide sequences, such as poly gly sequences of between about 5 and 200 amino acids. In some embodiments, proline residues are incorporated into the linker to prevent the formation of significant secondary structural elements by the linker. Preferred linkers are often flexible amino acid subsequences which are synthesized as part of a recombinant fusion protein comprising the RNA recognition domain. In one embodiment, the flexible linker is an amino acid subsequence comprising a proline such as Gly(x)-Pro-Gly(x) where x is a number between about 3 and about 100. In other embodiments, a chemical linker is used to connect synthetically or recombinantly produced recognition and labeling domain subsequences. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

The detectable labels used in the assays of the present invention, which are attached to the detection reagent, can be primary labels (where the label comprises an element that is detected directly or that produces a directly detectable element) or secondary labels (where the detected label binds to a primary label, e.g., as is common in immunological labeling). An introduction to labels, labeling procedures and detection of labels is found in Polak and Van Noorden (1997) *Introduction to Immunocytochemistry*, 2nd ed., Springer Verlag, NY and in Haugland (1996) *Handbook of Fluorescent Probes and Research Chemicals*, a combined handbook and catalogue Published by Molecular Probes, Inc., Eugene, Oreg. Primary and secondary labels can include undetected elements as well as detected elements. Useful primary and secondary labels in the present invention can include spectral labels such as fluorescent dyes (e.g., fluorescein and derivatives such as fluorescein isothiocyanate (FITC) and Oregon Green™, rhodamine and derivatives (e.g., Texas red, tetrarhodimine isothiocynate (TRITC), etc.), digoxigenin, biotin, phycoerythrin, AMCA, CyDyes™, and the like), radiolabels (e.g., $^3$H, $^{125}$I, $^{35}$S, $^{14}$C, $^{32}$P, $^{33}$P, etc.), enzymes (e.g., horse radish peroxidase, alkaline phosphatase etc.), spectral colorimetric labels such as colloidal gold or colored glass or plastic (e.g. polystyrene, polypropylene, latex, etc.) beads. The label may be coupled directly or indirectly to a component of the detection assay (e.g., the detection reagent) according to methods well known in the art. As indicated above, a wide variety of labels may be used, with the choice of label depending on sensitivity required, ease of conjugation with the compound, stability requirements, available instrumentation, and disposal provisions.

Preferred labels include those that use: 1) chemiluminescence (using horseradish peroxidase and/or alkaline phosphatase with substrates that produce photons as breakdown products as described above) with kits being available, e.g., from Molecular Probes, Amersham, Boehringer-Mannheim, and Life Technologies/Gibco BRL; 2) color production (using both horseradish peroxidase and/or alkaline phosphatase with substrates that produce a colored precipitate [kits available from Life Technologies/Gibco BRL, and Boehringer-Mannheim]); 3) hemifluorescence using, e.g., alkaline phosphatase and the substrate AttoPhos [Amersham] or other substrates that produce fluorescent products, 4) fluorescence (e.g., using Cy-5 [Amersham]), fluorescein, and other fluorescent tags]; 5) radioactivity. Other methods for labeling and detection will be readily apparent to one skilled in the art.

One preferred example of detectable secondary labeling strategies uses an antibody that recognizes DNA-RNA heterohybrid regions linked to an enzyme (typically by recombinant or covalent chemical bonding). The antibody is detected when the enzyme reacts with its substrate, producing a detectable product.

Preferred enzymes that can be conjugated to detection reagents of the invention include, e.g., β-galactosidase, luciferase, horse radish peroxidase, and alkaline phosphatase. The chemiluminescent substrate for luciferase is luciferin. One embodiment of a chemiluminescent substrate for β-galactosidase is 4-methylumbelliferyl-β-D-galactoside. Embodiments of alkaline phosphatase substrates include p-nitrophenyl phosphate (pNPP), which is detected with a spectrophotometer; 5-bromo-4-chloro-3-indolyl phosphate/nitro blue tetrazolium (BCIP/NBT) and fast red/napthol AS-TR phosphate, which are detected visually; and 4-methoxy-4-(3-phosphonophenyl) spiro[1,2-dioxetane-3,2'adamantane], which is detected with a luminometer. Embodiments of horse radish peroxidase substrates include 2,2'azino-bis(3-ethylbenzthiazoline-6 sulfonic acid) (ABTS), 5-aminosalicylic acid (5AS), o-dianisidine, and o-phenylenediamine (OPD), which are detected with a spectrophotometer; and 3,3,5,5'-tetramethylbenzidine (TMB), 3,3'diaminobenzidine (DAB), 3-amino-9-ethylcarbazole (AEC), and 4-chloro-1-naphthol (4C1N), which are detected visually. Other suitable substrates are known to those skilled in the art. The enzyme-substrate reaction and product detection are performed according to standard procedures known to those skilled in the art and kits for performing enzyme immunoassays are available as described above.

In general, a detector which monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeling moieties is digitized for subsequent computer analysis.

Most typically, primase activity is measured by quantitating the amount of label fixed to the solid support by binding of the detection reagent. Typically, presence of a modulator during incubation will increase or decrease the amount of label fixed to the solid support relative to a control incubation which does not comprise the modulator, or as compared to a baseline established for a particular reaction type. Means of detecting and quantitating labels are well known to those of skill in the art. Thus, for example, where the label is a radioactive label, means for detection include a scintillation counter or photographic film as in autoradiography. Where the label is optically detectable, typical detectors include microscopes, cameras, phototubes and photodiodes and many other detection systems which are widely available.

Primase Activity Modulators

The invention also provides methods of identifying compounds that modulate primase activity. Essentially any chemical compound can be used as a potential primase activity modulator in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial library containing a large number of potential therapeutic compounds (potential modulator compounds). Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (PCT Publication No. WO 91/19735), encoded peptides (PCT Publication WO 93/20242), random biooligomers (PCT Publication No. WO 92/00091), benzodiazepines (U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with β-D-glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see, Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309–314 (1996) and PCT/US96/10287), carbohydrate libraries (see, e.g., Liang et al., *Science*, 274:1520–1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

As noted, the invention provides in vitro assays for primase activity in a high throughput format. Control reactions that measure the activity of a primase in a reaction that does not include a primase activity modulator are optional, as the assays are highly uniform. Such optional control reactions are appropriate and increase the reliability of the assay. Accordingly, in a preferred embodiment, the methods of the invention include such a control reaction. For each of the assay formats described, "no modulator" control reactions which do not include a modulator provide a background level of activity for a given primase.

In some assays it will be desirable to have positive controls to ensure that the components of the assays are working properly. At least two types of positive controls are appropriate. First, a known activator of primase can be incubated with one sample of the assay, and the resulting increase in synthesis of RNA primers can be detected by measuring the resulting increase in nucleic acids having DNA-RNA heterohybrid regions according to the methods herein. Second, a known inhibitor of primase activity such as fludarabine triphosphate can be added, and the resulting decrease in primase activity similarly detected. It will be appreciated that modulators can also be combined with primase activators or inhibitors to find modulators which inhibit primase activation or repression that is otherwise caused by the presence of the known primase modulator.

In the high throughput assays of the invention, it is possible to screen up to several thousand different modulators in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (96) modulators. If 1536 well plates are used, then a single plate can easily assay from about 100- about 1500 different compounds. It is possible to assay several different plates per day; assay screens for up to about 6,000–20,000 different compounds is possible using the integrated systems of the invention.

Compositions, Kits and Integrated Systems

The invention provides compositions, kits and integrated systems for practicing the assays described herein. For example, an assay composition having a primase, nucleic acid template, a recognition reagent, and a labelling reagent is provided by the present invention. The invention also provides assay compositions for use in the solid phase assays; such compositions can include, for example, a nucleic acid template immobilized on a solid support, a primase, and a labelling reagent. In each case, the assay compositions can also include ribonucleotide triphosphates and additional reagents that are desirable for primase catalytic activity. Modulators of primase activity can also be included in the assay compositions.

The invention also provides kits for practicing the primase assay methods noted above. The kits can include any of the compositions noted above, and optionally further include additional components such as instructions to practice a high-throughput method of assaying for primase activity, or screening for a primase inhibitor, one or more containers or compartments (e.g., to hold primase enzyme, nucleic acids, or the like), a control primase activity modulator, a robotic armature for mixing kit components or the like.

The invention also provides integrated systems for high-throughput screening of potential primase modulators for an effect on a primase. The systems typically include a robotic armature which transfers fluid from a source to a destination, a controller which controls the robotic armature, a label detector, a data storage unit which records label detection, and an assay component such as a microtiter dish comprising a well having a reaction mixture or a substrate comprising a fixed nucleic acid or immobilization moiety.

A number of robotic fluid transfer systems are available, or can easily be made from existing components. For example, a Zymate XP (Zymark Corporation; Hopkinton, Mass.) automated robot using a Microlab 2200 (Hamilton; Reno, N.V.) pipetting station can be used to transfer parallel samples to 96 well microtiter plates to set up several parallel simultaneous primase reactions.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical image, e.g., using PC (Intel x86 or Pentium chip-compatible DOS™, OS2™ WINDOWS™, WINDOWS NT™ or WINDOWS95™ based computers), MACINTOSH™, or UNIX based (e.g., SUN™ work station) computers.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. The apparatus and methods of the invention are easily used for viewing any sample, e.g., by fluorescent or dark field microscopic techniques.

EXAMPLES

The following examples are offered to illustrate, but not to limit the present invention.

Example 1

High Throughput Solution-phase Assay for DnaG Primase Activity using Heterohybrid-Specific Antibody This Example describes a solution-phase assay for DnaG primase activity as illustrated in FIG. 1. The assay employs an antibody specific for DNA-RNA heterohybrid regions as a recognition reagent. An unlabeled recognition reagent is used to immobilize the DNA-RNA heterohybrid regions and a second, labeled, recognition reagent (an enzyme-linked antibody specific for DNA-RNA heteroduplexes) is used to detect the presence of the DNA-RNA heterohybrid regions.

| Reagents | |
|---|---|
| Reaction Buffer (for DnaG primase) | Antibody solution |
| 50 mM Hepes, pH 7.5<br>100 mM potassium glutamate, pH 7.5<br>10 mM DTT | 20 μg/ml heterohybrid-specific,<br>affinity purified, polyclonal<br>antibody in PBS |

-continued

| Reagents |
|---|
| 5 mM magnesium acetate<br>0.1 mM each of ATP, CTP, GTP, UTP<br>Blocking buffer: |
| 5% BSA<br>0.5% Tween 20 in PBS |

Preparation of Assay Plates
1. Coat plates with 120 μl of stock antibody solution per well overnight at 4° C.
2. Wash twice with 200 μl PBS
3. Block with 150 μl of blocking buffer
4. Wash twice with 200 μl PBS Assay Steps
1. Add 80 μl of reaction buffer
2. Add 10 μl of DMSO
3. Add 10 μl of 17 nM DnaG plus 0.5 pmoles of alkaline-denatured plasmids (100 ng) in Primase Reaction Buffer without the nucleotides. To determine the background signal, add 90 μl of Primase Reaction Buffer and 10 μl of DMSO only (No DnaG in these wells).
4. Incubate at room temperature for 1 hour
5. Wash three times with deionized water
6. Add 100 μl alkaline phosphatase-coupled heterohybrid-specific antibody
7. Incubate at room temperature for 45 minutes
8. Wash three times with deionized water
9. Add 100 μl chemiluminescent substrate
10. Shake for ten minutes and read on the liminometer.

Example 2

Figure 2:
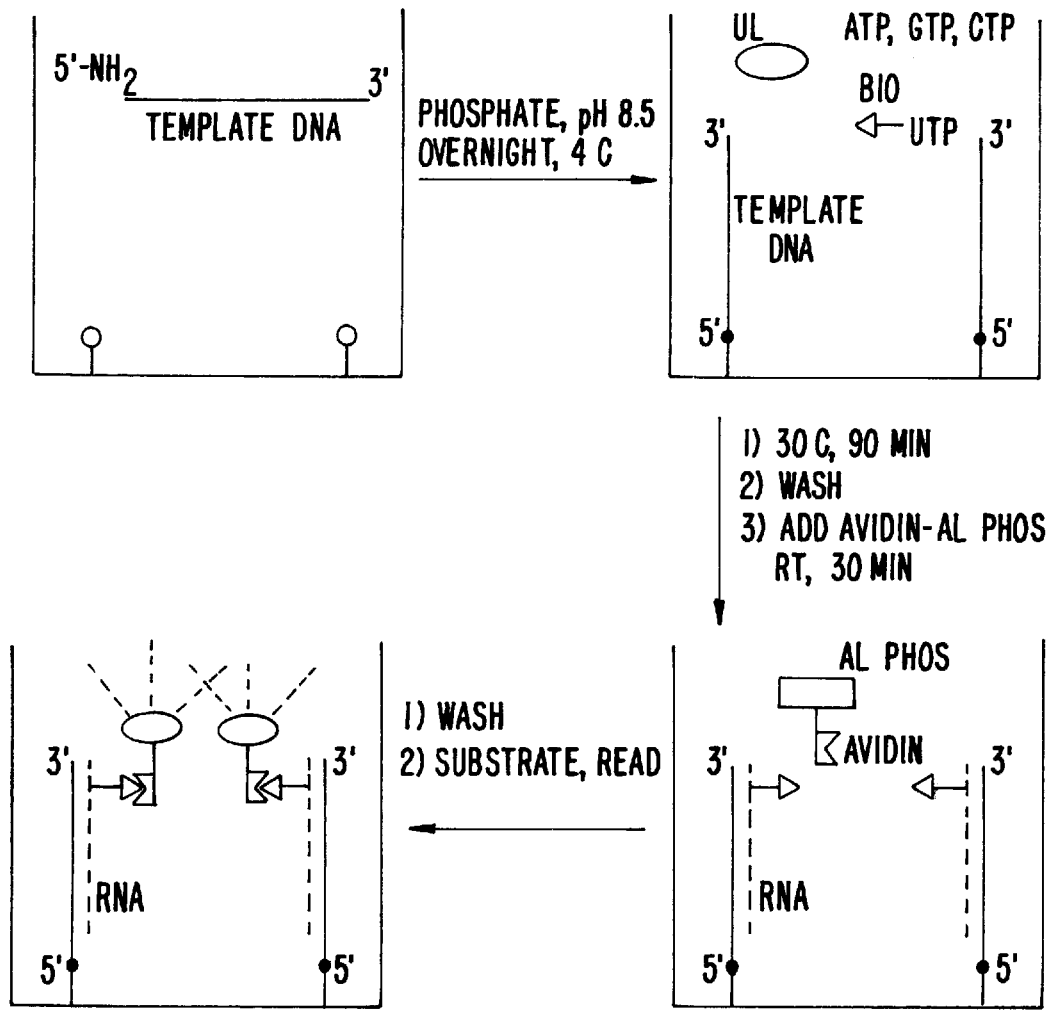
FIG. 2 shows a schematic diagram of a solid-phase chemiluminescence assay for UL5/8/52 primase activity. Template DNA is pre-immobilized to DNA-Bind plates (Costar) by incubation in phosphate buffer (pH 8.5) overnight at 4° C. The reaction mixture which includes a UL5/8/52 primase, ATP, GTP, and CTP, as well as biotinylated UTP, is then added to the wells. The mixture is incubated for 90 minutes at 30° C. The plate is then washed, and an avidin-coupled alkaline phosphatase detection reagent is added. After a 30 minute incubation at room temperature, the plate is again washed, and bound enzyme activity is measured by chemiluminescence.

High Throughput Solid-phase Assay for HSV Helicase-Primase Activity using Biotinylated Ribonucleotides This Example describes a solid-phase high throughput assay for screening for potential modulators of HSV-helicase primase activity (UL5/8/52), using a protocol similar to that illustrated in FIG. 2. The assay employs an immobilized DNA template, and RNA primers synthesized by the primase are detected by use of a detection reagent that binds to biotinylated ribonucleotides that are incorporated into the primers.

| Reagents | |
|---|---|
| Reaction Buffer (for HSV Primase) | 10X Nucleotide mix: |
| 100 mM Tris, pH 8.0<br>50 mM NaCl<br>1 mM DTT<br>200 μg/ml BSA (Fraction V)<br>10% glycerol<br>4 mM MgCl$_2$<br>Wash buffer: | 10 mM ATP<br>10 mM GTP<br>1 mM CTP<br>20 μM Bio-UTP<br>Biotinylated-UTP: Cat # 1 388 908<br>(Boehringer)<br>Coupling buffer: |
| 0.1 M Tris, pH 7.5<br>0.15 M NaCl<br>0.05% Tween20<br>0.5% NP40 | 0.05 M PO$_4$ pH 8.5, 1 mM EDTA |

-continued

| Reagents | |
|---|---|
| Avidin-alkaline phosphatase dilution buffer: | |
| 25 mM Hepes, pH 7.6 | |
| 0.5 M NaCl | |
| 0.1% BSA (Recrystallized, NOT Fraction V; Sigma, # A3803) | |

The DNA template used in this assay has an amino group at the 5' end to allow coupling to the plate. The sequence of the template, $NH_2$-pA-299 (Operon) is: $NH_2$-5'-AAA AAA AAA AAA AAA AAA CTT CTT CCC TTC CTA CTA CCC TCC CGC TCT TCC TCT CTT CTT TCT CCT TT (SEQ ID NO:1).

Assay Steps

NOTE: Only autoclaved water should be used in the assay.

1. Add 100 µl DNA template (0.075 pmol/µl) in coupling buffer to DNA-Bind plates (Costar, cat # 2499). Coupling can be done for 60 minutes at 37° C., or overnight at 4° C. Decant and tap dry on paper towel.
2. 80 µl buffer containing nucleotide mix (7 vol reaction buffer+1 vol 10× Nucleotide mix).
3. Add 10 µl DMSO or potential activity modulator compound in DMSO.
4. Add 10 µl 12.5 ng/µl UL5/8/52 in reaction buffer=125 ng/well.
5. Incubate at room temperature for 60 min.
6. Wash 5× with wash buffer.
7. Add 100 µl Avidin-alkaline phosphatase (Avidin-Al Phos) (Pierce# 21321). The stock solution is made by adding 1 ml of water to the source vial. Dilute this 100-fold in Avidin-Al Phos dilution buffer to get the working solution. Each well thus has 1 µl of stock Avidin-Al Phos.
8. Shake for 30 min at room temperature.
9. Wash 5× with wash buffer.
10. Add 100 µl of Al Phos substrate (CSPD, Tropix, cat# CD500RX).
11. Read in luminometer.

Example 3

High Throughput Solid-phase Assay for dnaG Primase using Heterohybrid-Specific Antibody This Example describes a solid-phase assay for screening for modulators of dnaG primase activity. This assay employs an antibody that is specific for DNA-RNA heterohybrid regions as the detection moiety.

| Reagents | |
|---|---|
| Reaction Buffer (for DnaG Primase) | 10X Nucleotide mix: |
| 100 mM Tris, pH 8.0 | 10 mM ATP |
| 50 mM NaCl | 10 mM GTP |
| 1 mM DTT | 10 mM CTP |
| 200 µg/ml BSA (Fraction V) | 10 µM UTP |
| 10% glycerol | |
| 4 mM $MgCl_2$ | |

-continued

| Reagents | |
|---|---|
| Wash buffer | Coupling buffer: |
| 0.1 M Tris, pH 7.5 | 0.05 M $PO_4$ pH 8.5, +1 mM EDTA |
| 0.15 M NaCl | |
| 0.05% Tween20 | |
| 0.5% NP40 | |
| Alkaline phosphatase antibody dilution buffer: | |
| 25 mM Hepes, pH 7.6 | |
| 0.5 M NaCl | |
| 0.1% BSA (Recrystallized, NOT Fraction V; Sigma, # A3803) | |

This assay uses a DNA template that has an amino group at the 5' end to allow coupling to the plate. The sequence of the template, GO604 (Operon), is: $NH_2$-5' GGA CGG CGA AAG CCG CCG TCC CTA CTG CAA AGC CAA AAG GAC (SEQ ID NO:2)

Assay Steps

NOTE: Use only autoclaved water.

1. Add 100 µl DNA template (0.075 pmol/µl) in coupling buffer to DNA-Bind plates (Costar, cat# 2499). Coupling can be done for 60 minutes at 37° C., or overnight at 4° C. Decant and tap dry on paper towel.
2. 80 µl buffer containing nucleotide mix (7 vol reaction buffer+1 vol 10× Nucleotide mix).
3. Add 10 µl DMSO or potential activity modulator compound in DMSO.
4. Add 10 µl 12.5 ng/µl DnaG Primase in reaction buffer= 125 ng/well.
5. Incubate at room temperature for 60 min.
6. Wash 5× with wash buffer.
7. Add 100 µl of alkaline phosphatase-coupled heterohybrid-specific antibody. The stock solution is made by adding 1 ml of water to the source vial. Dilute this 100-fold in Al Phos dilution buffer to get the working solution. Each well thus has 1 µl of stock Al Phos.
8. Shake for 30 min at room temperature.
9. Wash 5× with wash buffer.
10. Add 100 µl of Al Phosph substrate (CSPD, Tropix, cat# CD500RX).
11. Read in luminometer.

Example 4

High Throughput Assay for CMV Helicase Primase using Heterohybrid-Specific Antibody This Example describes a solid-phase assay for screening for potential modulators of cytomegalovirus helicase primase activity. The assay employs an antibody that specifically binds to DNA-RNA heterohybrid regions as a detection reagent.

| Reagents | |
|---|---|
| Reaction Buffer (for CMV Helicase Primase) | 10X Nucleotide mix: |
| 100 mM Tris, pH 8.0 | 10 mM ATP |
| 50 mM NaCl | 10 mM GTP |

-continued

| Reagents | |
|---|---|
| 1 mM DTT | 10 mM CTP |
| 200 μg/ml BSA (Fraction V) | 10 μM UTP |
| 10% glycerol | |
| 4 mM MgCl₂ | Alkaline phosphatase |
| Wash buffer | antibody dilution buffer: |
| 0.1 M Tris, pH 7.5 | 25 mM Hepes, pH 7.6 |
| 0.15 M NaCl | 0.5 M NaCl |
| 0.05% Tween20 | 0.1% BSA (Recrystallized, |
| 0.5% NP40 | NOT Fraction V; Sigma, # A3803) |

This assay uses sheared salmon sperm DNA as the DNA template.

Assay Steps

NOTE: Use only autoclaved water.

1. Add 100 μl DNA template (0.075 pmol/μl) in PBS to polylysine-coated glass plates. Bake in a dry vacuum oven for 4 hrs at 80° C. and rinse 5× with PBS. Decant and tap dry on paper towel.
2. 80 μl buffer containing nucleotide mix (7 vol reaction buffer+1 vol 10× Nucleotide mix).
3. Add 10 μl DMSO or potential activity modulator compound in DMSO.
4. Add 10 μl 12.5 ng/μl CMV Primase in reaction buffer= 125 ng/well.
5. Incubate at room temperature for 60 min.
6. Wash 5× with wash buffer.
7. Add 100 μl of alkaline phosphatase-coupled heterohybrid-specific antibody. The stock solution is made by adding 1 ml of water to the source vial. Dilute this 100-fold in Al Phos dilution buffer to get the working solution. Each well thus has 1 μl of stock Al Phos.
8. Shake for 30 min at room temperature.
9. Wash 5× with wash buffer.
10. Add 100 μl of Al Phos substrate (CSPD, Tropix, cat# CD500RX).
11. Read in luminometer.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method for measuring the activity of a primase, the method comprising the steps of:
 incubating a mixture comprising a DNA template, a primase, and ribonucleotide triphosphates under conditions in which the primase polymerizes the triphosphates on the template to form a nucleic acid comprising one or more DNA-RNA heterohybrid regions;
 contacting the nucleic acid with a recognition reagent that comprises a tag and a moiety which specifically binds to a DNA-RNA heterohybrid region;
 binding the tag to a solid support; and
 detecting the presence of DNA-RNA heterohybrid regions immobilized on the solid support.

2. The method of claim 1, wherein the DNA-RNA heterohybrid regions are not adjacent to a promoter region in the DNA template.

3. The method of claim 1, wherein the method further comprises the step of quantitating the amount of DNA-RNA heterohybrid regions bound to the solid support.

4. The method of claim 1, wherein the reaction mixture comprises one or more ribonucleotide triphosphates which comprise a label and the presence of DNA-RNA heterohybrid regions is detected by determining whether the nucleic acid comprises labeled ribonucleotide triphosphates.

5. The method of claim 1, wherein the reaction mixture comprises one or more ribonucleotide triphosphates which comprise a hapten and the presence of DNA-RNA heterohybrid regions is detected by contacting the nucleic acid with a detection reagent that binds to the hapten.

6. The method of claim 1, wherein the recognition reagent comprises an antibody which binds to DNA-RNA heterohybrids.

7. The method of claim 6, wherein the antibody does not bind to DNA-DNA homoduplexes.

8. The method of claim 1, wherein the DNA-RNA heterohybrid regions are detected by binding a detection reagent to the nucleic acid, wherein the detection reagent is directly or indirectly detectable, and detecting the detection reagent.

9. The method of claim 8, further comprising removing unbound detection reagent by washing the unbound detection reagent from the solid substrate, wherein the unbound detection reagent is not bound to the DNA-RNA heterohybrid region.

10. The method of claim 8, wherein the detection reagent comprises an antibody which binds to DNA-RNA heterohybrids.

11. The method of claim 8, wherein the detection reagent comprises a detectable label.

12. The method of claim 11, wherein the detectable label comprises an alkaline phosphatase label and the method further comprises adding an alkaline phosphatase substrate to the detection reagent.

13. The method of claim 1, wherein the method comprises parallel repetition of the reaction steps in a microtiter format.

14. A method for measuring the activity of a primase, the method comprising the steps of:
 providing a DNA template immobilized on a solid support;
 contacting the DNA template with a reaction mixture comprising a primase and ribonucleotide triphosphates under conditions in which the primase polymerizes the triphosphates on the template to form a nucleic acid comprising one or more DNA-RNA heterohybrid regions; and
 detecting the presence of DNA-RNA heterohybrid regions bound to the solid support.

15. The method of claim 14, wherein the method further comprises the step of quantitating the amount of DNA-RNA heterohybrid regions bound to the solid support.

16. The method of claim 14, wherein the DNA-RNA heterohybrid regions are not adjacent to a promoter region in the DNA template.

17. The method of claim 14, wherein the reaction mixture comprises one or more ribonucleotide triphosphates which comprise a label and the presence of DNA-RNA heterohybrid regions is detected by determining whether the nucleic acid comprises labeled ribonucleotide triphosphates.

18. The method of claim 14, wherein the reaction mixture comprises one or more ribonucleotide triphosphates which comprise a hapten and the presence of DNA-RNA heterohybrid regions is detected by contacting the nucleic acid with a detection reagent that binds to the hapten.

19. The method of claim 14, wherein the presence of DNA-RNA heterohybrid regions is detected by contacting the nucleic acid with a detection reagent which binds to the DNA-RNA heterohybrid regions and detecting the amount of detection reagent bound to the DNA-RNA heterohybrid regions.

20. The method of claim 19, wherein the detection reagent comprises an antibody that binds to DNA-RNA-heterohybrid nucleic acids.

21. The method of claim 20, wherein the recognition reagent does not bind to DNA-DNA homoduplexes.

22. The method of claim 20, wherein the recognition reagent comprises a detectable label.

23. The method of claim 22, wherein the detectable label comprises an alkaline phosphatase label and the method further comprises adding an alkaline phosphatase substrate to the detection reagent.

24. The method of claim 14, wherein the method comprises parallel repetition of the reaction steps in a microtiter format.

25. The method of claim 1 or 14 wherein the reaction mixture further comprises a potential modulator of primase activity.

26. The method of claim 25, wherein the solid support is selected from the group consisting of a bead, a membrane, and a 96-well plate.

27. The method of claim 25, wherein the method comprising repeating the method steps in parallel in a microtiter plate format, wherein at least about 1,000 different potential activity modulators are tested for an effect on primase activity.

28. The method of claim 27, wherein at least about 1,000 different potential activity modulators are tested for an effect on primase activity in one day.

* * * * *